US012596063B2

(12) United States Patent
Van Der Sluis

(10) Patent No.: US 12,596,063 B2
(45) Date of Patent: Apr. 7, 2026

(54) COOKING SYSTEM, INCLUDING A PARTICLE DETECTING APPARATUS, AND A COOKING METHOD

(71) Applicant: KONINKLIJKE PHILIPS N.V., Eindhoven (NL)

(72) Inventor: Paul Van Der Sluis, Eindhoven (NL)

(73) Assignee: VERSUNI HOLDING B.V., Eindhoven (NL)

( * ) Notice: Subject to any disclaimer, the term of this patent is extended or adjusted under 35 U.S.C. 154(b) by 1119 days.

(21) Appl. No.: 17/052,819

(22) PCT Filed: May 22, 2019

(86) PCT No.: PCT/EP2019/063164
§ 371 (c)(1),
(2) Date: Nov. 4, 2020

(87) PCT Pub. No.: WO2019/228875
PCT Pub. Date: Dec. 5, 2019

(65) Prior Publication Data
US 2021/0131937 A1 May 6, 2021

(30) Foreign Application Priority Data

May 28, 2018 (EP) ..................................... 18174483

(51) Int. Cl.
*G01N 15/0205* (2024.01)
*A47J 37/06* (2006.01)
(Continued)

(52) U.S. Cl.
CPC ...... *G01N 15/0205* (2013.01); *A47J 37/0664* (2013.01); *G01N 15/1459* (2013.01);
(Continued)

(58) Field of Classification Search
CPC ... A47J 37/0664; F24C 15/20; F24C 15/2007; F24C 15/2021; F24F 8/80; F24F 11/0001;
(Continued)

(56) References Cited

U.S. PATENT DOCUMENTS 4,223,559 A * 9/1980 Chuan .................... G08B 17/12
73/865.5
4,482,247 A 11/1984 Meltz
(Continued)

FOREIGN PATENT DOCUMENTS

EP 0462642 12/1991
WO 01/00073 1/2001
(Continued)

OTHER PUBLICATIONS

Spatial and temporal variability of the PM2.5/PM10 ratio in Wuhan, Central China; Xu, et al . . . Aerosol and Air Quality Research, 17: 741-751 (Year: 2017).*
(Continued)

*Primary Examiner* — Steven W Crabb
*Assistant Examiner* — Dilnessa B Belay
(74) *Attorney, Agent, or Firm* — Maschoff Brennan

(57) ABSTRACT

A cooking system combines a food cooking unit and a particle detection system. By deriving a ratio between particle concentrations in at least two size ranges, particular particles may be identified, and the food cooking unit may then be controlled to reduce or eliminate the generation of those particles.

15 Claims, 4 Drawing Sheets

(51) Int. Cl.

| | |
|---|---|
| *G01N 15/00* | (2024.01) |
| *G01N 15/14* | (2024.01) |
| *G01N 33/00* | (2006.01) |

(52) U.S. Cl.
CPC . *G01N 33/0009* (2013.01); *G01N 2015/0046* (2013.01); *G01N 2015/1486* (2013.01); *G01N 2015/1493* (2013.01)

(58) Field of Classification Search
CPC ................. F24F 11/30; G01N 15/0205; G01N 2015/0046; G01N 2015/486; G01N 2015/1493; G01N 15/06; G01N 15/075; G01N 2015/1486
See application file for complete search history.

(56) References Cited

U.S. PATENT DOCUMENTS

| | | | |
|---|---|---|---|
| 9,010,313 B2 | 4/2015 | Mikulec | |
| 2001/0052852 A1* | 12/2001 | Kouznetsov | F24C 14/02 |
| | | | 219/393 |
| 2011/0221889 A1 | 9/2011 | Knox | |
| 2018/0202667 A1* | 7/2018 | Cheng | H04N 23/74 |

FOREIGN PATENT DOCUMENTS

| | | | |
|---|---|---|---|
| WO | 2015/189089 | 12/2015 | |
| WO | 2016/198360 | 12/2016 | |
| WO | WO-2016198360 A1 * | 12/2016 | ......... G01N 15/1459 |

OTHER PUBLICATIONS

International Search Report and Written Opinion Dated Sep. 17, 2019 For International Application No. PCT/EP2019/063164 Filed May 22, 2019.

* cited by examiner

50

52

54

56

58

1

COOKING SYSTEM, INCLUDING A PARTICLE DETECTING APPARATUS, AND A COOKING METHOD

CROSS REFERENCE TO RELATED APPLICATIONS

This application is the U.S. National Phase application under 35 U.S.C. § 371 of International Application No. PCT/EP2019/063164 filed May 22, 2019, which claims the benefit of European Patent Application Number 18174483.0 filed May 28, 2018. These applications are hereby incorporated by reference herein.

FIELD OF THE INVENTION

This invention relates to a cooking apparatus and cooking method.

BACKGROUND OF THE INVENTION

It is well known that it is desirable to monitor pollution levels, such as particulate pollutants. Various sensing devices are known, which for example provide a particle concentration level for particles below a certain size. Optical particle sensing approaches are for example known based on optical scattering.

Industries, households, cars and trucks emit complex mixtures of air pollutants, many of which are harmful to health. Of all of these pollutants, fine particulate matter has the greatest effect on human health. Most fine particulate matter comes from fuel combustion, both from mobile sources such as vehicles and from stationary sources such as power plants, industry, households or biomass burning.

This invention is concerned in particular with the particular pollutants caused by cooking (i.e. biomass burning). It is well known that cooking produces undesirable odors and particles, and extractor fans are used to expel these odors and particles.

Fine particulate matter is associated with a broad spectrum of acute and chronic illness, such as lung cancer, chronic obstructive pulmonary disease (COPD) and cardiovascular diseases. Worldwide, it is estimated to cause about 25% of lung cancer deaths, 8% of COPD deaths, and about 15% of ischaemic heart disease and stroke. Particulate matter pollution is an environmental health problem that affects people worldwide, not only outdoors, but also indoors.

However, not all particulate matter is equally unhealthy. Salt spray created by wave action on seas for instance is completely harmless. It is especially the fine particles from combustion that cause harm, and these may for example result from biomass burning caused by cooking operations. There is therefore a need to obtain additional information on these particles and if possible reduce the generation of harmful particles. The generation of harmful particles in cooking is also indicative of the creation of harmful compounds in the food itself by the cooking process.

It is known that both a particle size and a particle size distribution of a pollutant may be used to identify a pollutant and hence the cause or source of the pollution.

Air pollution particle monitors give an indication in terms of PM2.5 or PM10. These estimate the total weight of particles suspended in air up to 2.5 or 10 μm. These numbers are highly relevant since air quality standards and air quality norms are based on such numbers. However, these numbers do not give information on the type of particles present, let alone on the health effect of these particles or the origin of these particles.

There is therefore a need for a system which is able to characterize particles, in particular to enable identification of particular particle types which may present a health risk or which may be indicative of other substances which themselves present a health risk, in particular caused by cooking operations.

SUMMARY OF THE INVENTION

The invention is defined by the claims.

According to examples in accordance with an aspect of the invention, there is provided a cooking system, comprising:

a food cooking unit; and a particle detection system for detecting particles, comprising:

a particle sensing unit, for determining particle concentrations in at least two size ranges; and a controller for processing the particle concentrations, wherein the controller is adapted:

to determine one or more ratios between the particle concentrations in the at least two size ranges; and in response to the determined one or more ratios, to provide an output for controlling the food cooking unit.

This cooking system makes use of an automatic control function when burning of food is detected. This food burning gives rise to a characteristic particle density profile, which can be detected based on a ratio between particles present in different size ranges. In this way, the harmful effects of these particles can be prevented by altering the cooking process. The presence of these particles is also indicative of the presence of harmful substances being created in the food, such as acrylamide and polycyclic aromatic hydrocarbons. By altering the cooking process the concentration of these compounds in the food can be minimized.

The use of a particle concentration ratio has been found to be far more effective in detecting the particular particles caused by food burning than by detecting absolute particle levels, since these absolute levels may be associated with many unknown variables, such as the distance between the sensing unit and cooking unit.

In particular, an increased (relative) prevalence of smaller particles is indicative of high temperatures and burning.

The ratio is for example between the concentrations for two different sizes (and a small range around that size), but it may instead may be obtained based on PM values (i.e. concentrations for all particles up to a given size threshold).

The controller may be adapted to control the food cooking unit to cease cooking or alter a cooking unit temperature setting. Thus, the cooking process may be adapted to reduce or halt the generation of harmful particles.

The controller may be further adapted, in response to the determined one or more ratios, to provide an output for controlling the operation of an air purifier.

As an additional measure, an air purifier may be controlled, for example turned on or driven to an increased fan speed, in response to the detection.

The particle detection system may then comprise part of the air purifier. Thus, there is a control link between an air purifier and a cooking unit, to provide an automated safety control feature for the cooking unit.

The first threshold size is for example 0.3 μm or 0.5 μm and/or the second threshold size is for example 1.0 μm or 2.5 μm. Thus, examples of possible ratios are 0.3 μm to 1.0 μm, or 0.3 μm to 2.5 μm, or 0.5 μm to 1.0 μm or 0.5 μm to 2.5 μm. Of course, these are just examples, and any desired ratio may be measured which best enables a target particle to be identified.

The food cooking unit may comprise an air fryer or a toaster. These are two examples of food cooking unit which may generate and release fine particulate matter.

The particle detection system may comprise:

an optical sensor which generates a sensor signal, wherein the sensor signal or an analysis of the sensor signal is controllable by applying a threshold setting, wherein the threshold setting dictates a particle size detection range captured by the sensor signal; and a controller, wherein the controller is adapted to apply at least first and second different threshold settings for determining the particle concentrations in the at least two size ranges, and to receive corresponding first and second optical sensor readings.

An optical sensing approach may be implemented at low cost.

The invention also provides a method of controlling a food cooking unit, comprising:

operating the food cooking unit to start cooking;

determining particle concentrations in at least two size ranges;

determining one or more ratios between the particle concentrations in the at least two size ranges; and in response to the determined one or more ratios, controlling the food cooking unit.

This method provides automated control of a cooking unit to reduce or prevent the generation of undesired particulate matter.

Controlling the food cooking unit may comprise ceasing cooking or altering a cooking unit temperature setting.

The method may also comprise, in response to the determined one or more ratios, controlling the operation of an air purifier. Thus, the method takes measures to reduce the concentration of particulate matter which has already been released, as well as reducing or eliminating the future generation of that particulate matter.

The particle detection system may then comprise part of the air purifier, so that there is an integrated cooking and air purification approach.

The first threshold size may be 0.3 μm or 0.5 μm and/or the second threshold size may be 1.0 μm or 2.5 μm.

The food cooking may comprise air frying or toasting.

The invention may be implemented at least in part in software.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a cooking system which combines a food cooking unit; and a particle detection system. By deriving a ratio between particle concentrations in at least two size ranges, particular particles may be identified, and the food cooking unit may then be controlled to reduce or eliminate the generation of those particles. The particles themselves may be harmful and/or they may be indicative of the generation of harmful substances in the cooked food.

Figure 1:
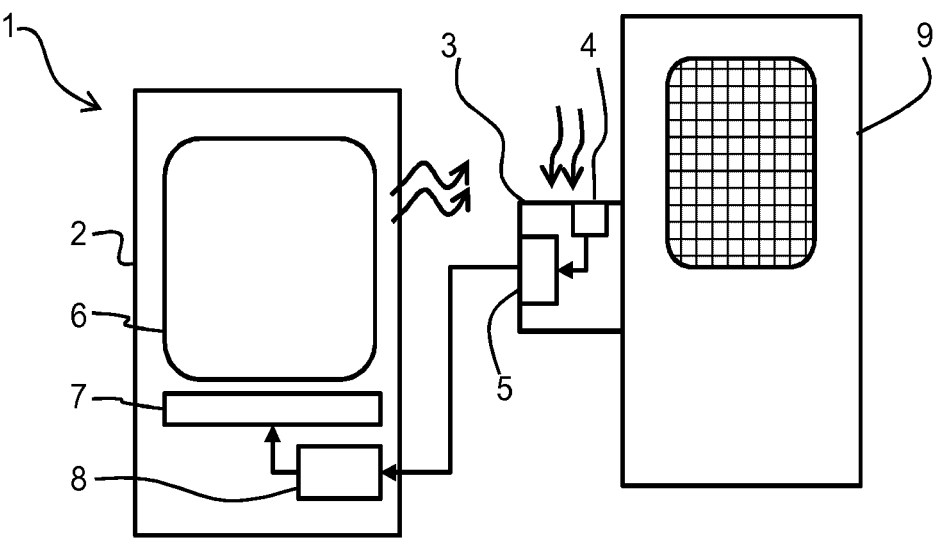
FIG. 1 shows a cooking system.

FIG. 1 shows a cooking system 1, comprising a food cooking unit 2 and a particle detection system 3 for detecting particles. The particle detection system 3 has a particle sensing unit 4 for determining particle concentrations in at least two size ranges and controller 5 for processing the particle concentrations.

The food cooking unit 2 comprises a food chamber or area 6, a heater 7 and a controller 8. The controller enables a cooking temperature to be set, typically both manually and electronically in an automated manner.

The controller 5 determines one or more ratios between the particle concentrations in at least two size ranges. This is used to identify particular particles. In response, an output is provided for controlling the food cooking unit 2 either to cease cooking or alter a cooking unit temperature setting.

The particle detection system 3 may be part of the cooking unit. However, in the example shown, it is part of an air purifier 9. This means the particle detection may be used to control the operation of the air purifier as well. The air purifier and the cooking unit are then preferably in the same general location (e.g. in the kitchen).

The food cooking unit 2 for example comprises an air fryer or a toaster. These are both able to burn food and hence release undesirable particulate matter.

An optical sensing system may be used to obtain the particle concentrations.

Figure 2:
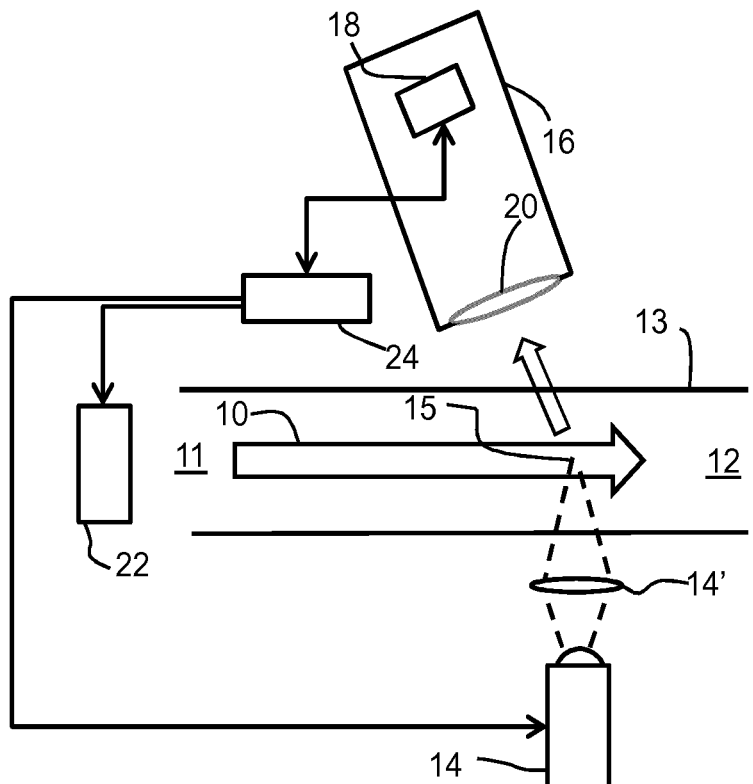
FIG. 2 shows an example of a particle sensor which may be employed in the cooking system.

FIG. 2 shows an example of a particle sensor which may be employed. There is a fluid (gas) flow 10 from an inlet 11 of a flow channel 13 to an outlet 12 of the flow channel 13. The flow channel 13 is formed by a conduit which has a length between the inlet 11 and outlet 12. The particles pass through a region which is irradiated by a light source 14 for providing light which is scattered by the particles to generate scattered light. Light from the light source 14 does not pass directly to the detector when particles are absent, and for this purpose the detector is at an angle to the light source path, as schematically shown in FIG. 2. The scattered light is detected by a light detector 16. A collimator 14' focuses the incident light from the light source 14 into a small measurement zone 15, for example in which only one particle is present at any moment to realize individual particle detection.

Thus, the sensor provides particle counting as well as individual particle sizing.

A flow control device 22, shown schematically in FIG. 2, is used for inducing flow through the particle sensor. It may comprise a fan, or a heater to create a convective heat flow. In a system using heating, the resulting buoyancy causes air to flow towards the top of the detector, carrying the particles through the flow channel. In such a case, the flow channel may be vertically upwards.

The light source is to one side of the flow channel 13 and the light detector 16 is on the opposite side. An alternative design may make use of the reflection of light. The light source may be a laser diode (e.g. pulsed laser) or an infrared LED.

The particles are irradiated in the measurement zone 15 at transparent portions of the conduit that defines the flow channel 13, which allow the light to pass through the conduit. The conduit may be part of a housing which is placed on a printed circuit board with the electronics to convert the signal due to the particles into a count. Leakage of incident light directly towards the photodiode light detector, which would give a background signal, is minimized.

The light detector 16 comprises a photodiode sensor 18 and a focusing lens 20 at which scattered light is detected thereby generating a light detector signal. The controller 24 controls the operation of the flow control device and light source.

For particle sizing, the detector signal may be amplified and compared with a threshold voltage. The threshold is implemented as a threshold voltage applied to a comparator which controls the particle size sensitivity of the sensor system.

Above a certain particle size, the peak height is sufficient to pass the threshold. The threshold thus implements a band pass filtering function. The pulse is counted to implement particle counting and the pulse length is measured to provide particle sizing. For a large set of detection pulses a measure of a low-pulse occupancy time (LPO %) is for example used.

Thus, there are two basic outputs. One is a simple particle count, which is a count of the number of detection peaks which exceed the threshold set. The other is an amplitude of an analog signal, which is proportional to the particle size.

For detecting a stream of particles, the sensor may be used to perform size binning. The threshold voltage provided to the comparator sets the boundary limit for the analog signal. For example, a 1V threshold means that all signals above 1V will be registered as a detection signal, hence corresponding to all particle sizes that generate an analog signal above 1V. Likewise, a 2V threshold raises the boundary for allowing only larger sized particles to generate an output.

For simplicity a 1V threshold voltage may correspond to signals generated for particles of 1 μm diameter and above, whereas as 2V threshold may correspond to particles of 2 μm diameter and above. In order to generate particle count information for a specific particle size range (also known as a 'size bin'), for a particle size range between 1 μm and 2 μm, the number of signals generated at these threshold voltages are subtracted.

Thus, the optical scattering sensor may be used for measuring individual particle sizes in an analog manner, or for recording particle sizes into bins in a more digital manner. Concentration levels in those bins may then be obtained.

Further details of the design and operation of optical particle sensors of this type will be well known to those skilled in the art.

The invention is based on using particle concentration ratios to identify types of particle, and control cooking accordingly. In particular, a ratio of small particle concentration to large particle concentration gives information on the type of particles present.

During normal cooking, such as frying or toasting, particles are emitted, but when the food starts to burn, a disproportionate number of small particles is emitted. Just looking at the absolute number is of no assistance because it depends on the amount of food, the distance between the measurement device and the cooker, the ventilation level of the room etc.

Figure 3:
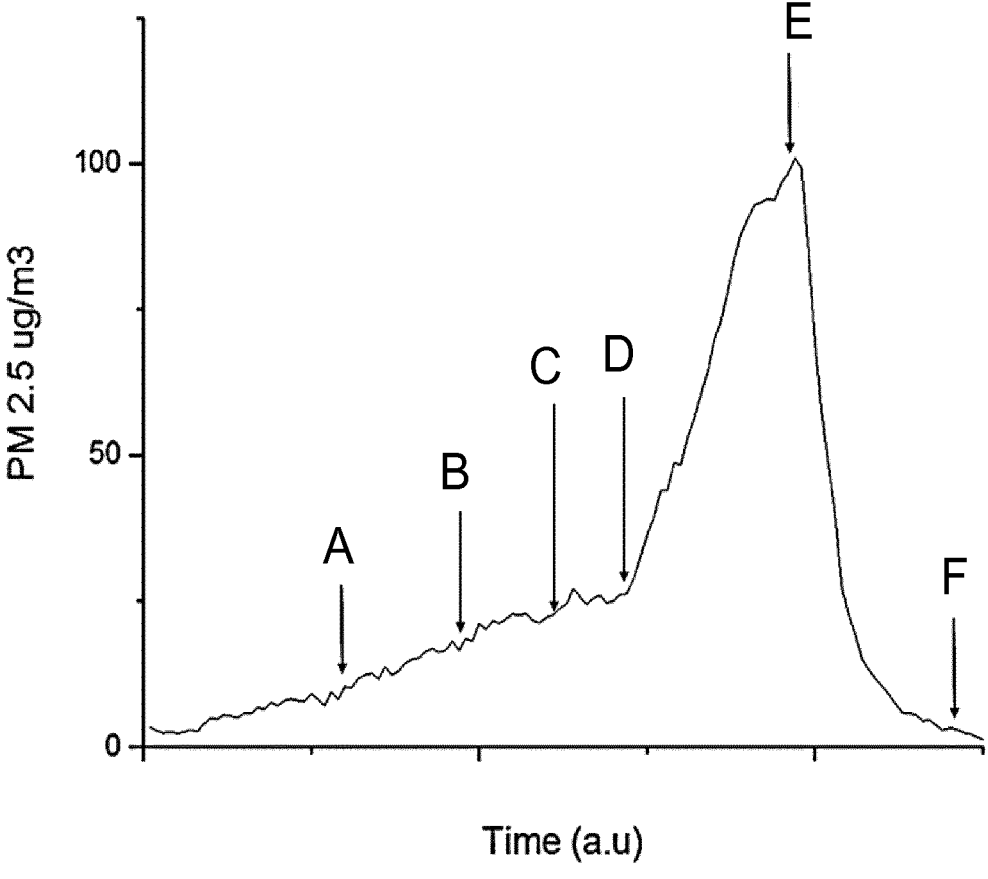
FIG. 3 shows the recorded PM 2.5 particle concentration during a frying process of an air fryer.

FIG. 3 shows the recorded PM 2.5 particle concentration during a frying process of an air fryer. The y-axis plots the particle concentration and the x-axis plots time (arbitrary units). The PM 2.5 levels slowly rise when the air fryer is switched on and when food is fried at the intended temperature. For example, at time A, the air fryer is at 170 degrees Celsius with no food content. The PM 2.5 emissions dramatically rise when the temperature is increased (to values at which the food may become burnt). For example, at time B, the air fryer is at 200 degrees Celsius. The concentrations have risen even though no food is present.

At time C, the air fryer is at 170 degrees Celsius with food added. At time D, the air fryer is at 200 degrees Celsius with food added.

At time E, the cooking is completed and the air fryer is turned off. The concentration levels drop continuously to time F.

However, the concentration levels themselves cannot be used as an indicator of the levels of hazardous particulate matter because they depend on the amount of food, the distance between the measurement device and the air fryer, the ventilation level of the room etc. Also at the end of the process (at time F) the PM 2.5 levels are low. However, a large number of the small hazardous particles are still present, but they do not show up in the PM 2.5 values because of their low weight.

During the burning of food, more small particles than large particles are emitted. So when the number of 0.5 μm particles is divided by the number of 1 μm particles, a peak is observed only when the food is getting too hot. This peak is a ratio, hence does not depend on the amount of food, the distance between the measurement device and air fryer, ventilation level of the room etc.

Figure 4:
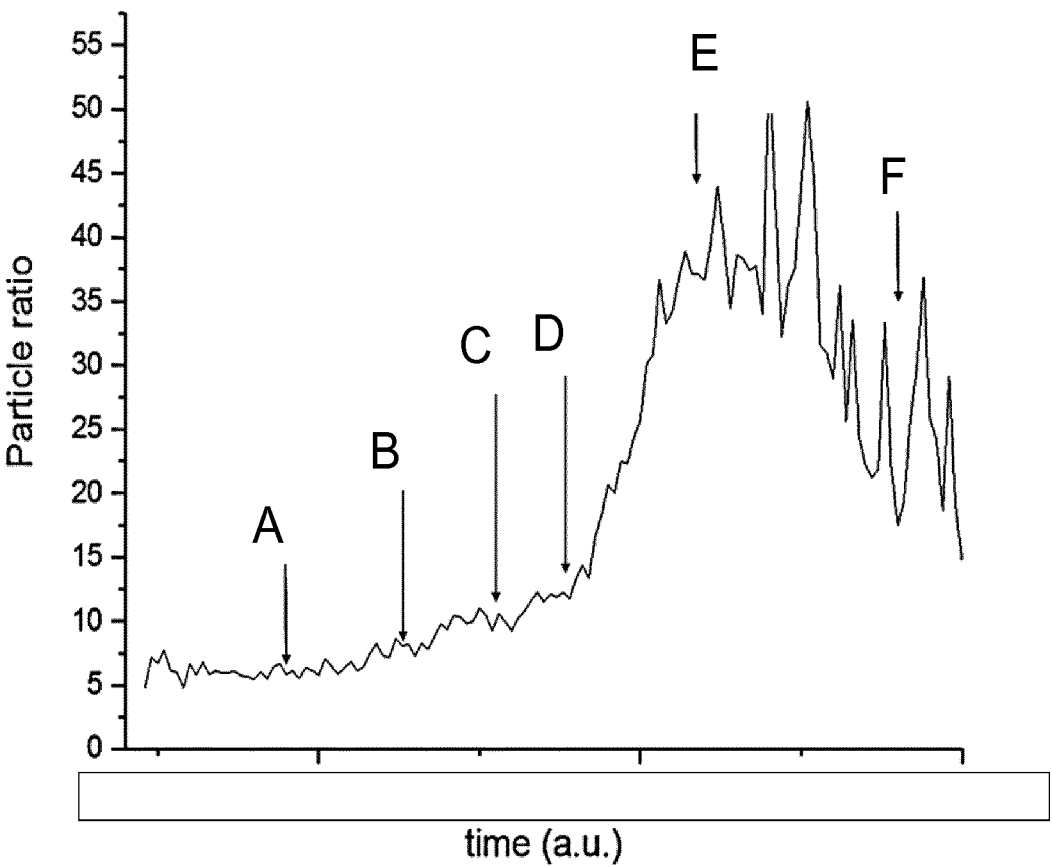
FIG. 4 shows a plot of a concentration ratio between 0.5 μm particles and 1.0 μm particles for the same process as FIG. 3.

FIG. 4 shows a plot of the concentration ratio (between 0.5 μm particles and 1.0 μm particles). It shows the same time points as FIG. 3.

The concentration ratio provides a much better indicator of the presence of hazardous particles. In response, the air fryer can automatically be switched off or set to a lower temperature when the particle ratio increases above a certain value (e.g. 15 in the example of FIG. 4).

Moreover, the concentration ratio is still high at the end of the process (time F), indicating the continuing dangerous levels of small combustion particles whereas the classical PM 2,5 values are low.

Other ratios can also be used, for instance 0.3 μm/1 μm or 0.3 μm/2.5 μm or 0.5 μm/2.5 μm.

More advanced optical sensors (such as self-mixing-interference sensors) are able to give information down to smaller sizes (such as 0.1 μm). The greater the range of sensitivity of the particle sensor, the greater the ability to detect particular particle types.

Figure 5:
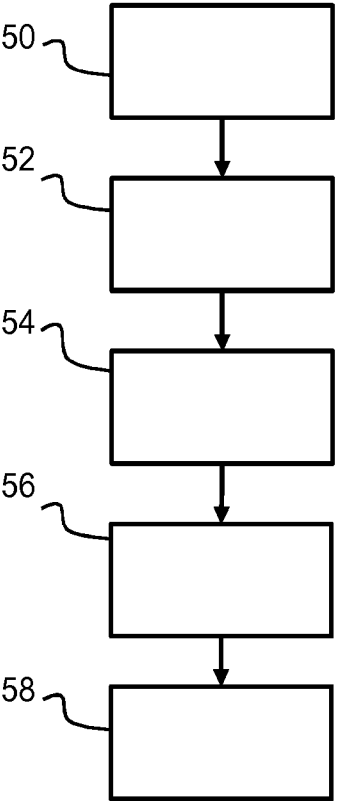
FIG. 5 shows a method of controlling a food cooking unit.

FIG. 5 shows a method of controlling a food cooking unit, comprising:

in step 50, operating the food cooking unit to start cooking;

in step 52, determining particle concentrations in at least two size ranges;

in step 54, determining one or more ratios between the particle concentrations in the at least two size ranges; and in response to the determined one or more ratios, in step 56, controlling the food cooking unit.

The method may also comprise in step 58 controlling the operation of an air purifier.

The invention is of interest for the detection food which has been burnt in a cooking unit such as a toaster or air fryer. It may of course be applied to other cooking units such as ovens.

As discussed above, embodiments make use of a controller 5. The controller can be implemented in numerous ways, with software and/or hardware, to perform the various functions required. A controller may use a microprocessor which is programmed using software (e.g., microcode) to perform the required functions. A controller may however be implemented with or without employing a microprocessor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

The example above is based on determining a ratio between different concentrations at different sizes. Basically, this gives crude measure of a particle distribution. A less crude measure may be obtained by monitoring more ratios. However, the use of a set of one or more ratios avoids the need for a full concentration distribution analysis. However, any number of ratios may be analyzed, thus the analysis may approach the information of a full concentration distribution, which may be interpreted by a finding a best fit function or by using a lookup table.

The size ranges for which concentration levels are obtained may have various different widths. For example a size range may be for the lowest particle size for which the sensor is sensitive up to a threshold (e.g. 0.1 μm to 0.5 μm) or it may be for a narrow size range around the size of interest, such as X μm±10% or X μm±10%, for example 0.5 μm±0.05 μm or 1 μm±0.1 μm. It will be seen that various different ratios are able to give a crude measure of a particle distribution function which is sufficient to detect when burning is taking place.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A cooking system, comprising:
a food cooking unit; and
a particle detection system adapted to detect particles, comprising:
an optical sensor adapted to generate a sensor signal;
a particle sensing unit adapted to determine particle concentrations in at least two size ranges; and
a controller adapted to process the particle concentrations,
wherein the controller is adapted to:
apply at least first and second different threshold settings when generating the sensor signal to determine the particle concentrations in the at least two size ranges;
determine a set of one or more ratios between the particle concentrations in the at least two size ranges; and
in response to the determined set of one or more ratios, identify types of particles and provide an output to control the food cooking unit.

2. The system as claimed in claim 1, wherein the controller is adapted to control the food cooking unit to cease cooking or alter a cooking unit temperature setting.

3. The system as claimed in claim 1, wherein the controller is further adapted, in response to the determined set of one or more ratios, to provide an output for controlling the operation of an air purifier.

4. The system as claimed in claim 3, wherein the particle detection system comprises part of the air purifier.

5. The system as claimed in claim 1, wherein a first threshold size is 0.3 μm or 0.5 μm and/or a second threshold size is 1.0 μm or 2.5 μm.

6. The system as claimed in claim 1, wherein the food cooking unit comprises an air fryer or a toaster.

7. The system as claimed in claim 1, wherein:
the sensor signal or an analysis of the sensor signal is controllable by applying a threshold setting, wherein the threshold setting dictates a particle size detection range captured by the sensor signal; and
the controller is further adapted to receive corresponding first and second optical sensor readings.

8. A method of controlling a food cooking unit, comprising:
operating the food cooking unit to start cooking;
determining particle concentrations in at least two size ranges, wherein determining the particle concentrations comprises applying at least first and second different threshold settings when generating an optical sensor signal;
determining a set of one or more ratios between the particle concentrations in the at least two size ranges; and
in response to the determined set of one or more ratios, identifying types of particles and controlling the food cooking unit.

9. The method as claimed in claim 8, wherein controlling the food cooking unit comprises ceasing cooking or altering a cooking unit temperature setting.

10. The method as claimed in claim 8, comprising, in response to the determined set of one or more ratios, controlling the operation of an air purifier.

11. The method as claimed in claim 10, wherein the particle detection system comprises part of the air purifier.

12. The method as claimed in claim 8, wherein a first threshold size is 0.3 μm or 0.5 μm and/or a second threshold size is 1.0 μm or 2.5 μm.

13. The method as claimed in claim 8, wherein the food cooking comprises air frying or toasting.

14. The method as claimed in claim 8, wherein the threshold setting dictates a particle size detection range captured by the optical sensor signal, thereby determining the particle concentrations in the at least two size ranges.

15. A non-transitory computer readable storage medium comprising a computer program, wherein the computer program comprises computer code which is adapted, when run on a computer, to implement the method of claim 8.

\* \* \* \* \*